T

United States Patent
Fujii et al.

(10) Patent No.: US 7,015,252 B2
(45) Date of Patent: Mar. 21, 2006

(54) COMPOSITIONS FOR LESSENING OXIDATIVE STRESS

(75) Inventors: Kenji Fujii, Kobe (JP); Taizo Kawabe, Himeiji (JP); Kazunori Hosoe, Takasago (JP); Takayoshi Hidaka, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/492,164

(22) PCT Filed: Oct. 15, 2002

(86) PCT No.: PCT/JP02/10641

§ 371 (c)(1),
(2), (4) Date: Apr. 9, 2004

(87) PCT Pub. No.: WO03/032968

PCT Pub. Date: Apr. 24, 2003

(65) Prior Publication Data

US 2004/0248991 A1    Dec. 9, 2004

(30) Foreign Application Priority Data

Oct. 12, 2001   (JP) .............................. 2001-314932

(51) Int. Cl.
*A61K 31/12*   (2006.01)

(52) U.S. Cl. .................................... 514/690

(58) Field of Classification Search ................ 514/690

See application file for complete search history.

(56) References Cited

U.S. PATENT DOCUMENTS

| | | | | | |
|---|---|---|---|---|---|
| 5,059,627 A | * | 10/1991 | Goto et al. | ................. | 514/688 |
| 6,133,322 A | * | 10/2000 | Rustin et al. | ................. | 514/689 |
| 6,184,255 B1 | | 2/2001 | Mae et al. | | |
| 6,303,139 B1 | * | 10/2001 | Passi et al. | ................. | 424/441 |
| 6,740,338 B1 | * | 5/2004 | Chopra | ..................... | 424/456 |

FOREIGN PATENT DOCUMENTS

| | | |
|---|---|---|
| WO | WO 98/07417 A1 | 2/1998 |
| WO | WO 00/57871 A2 | 10/2000 |

OTHER PUBLICATIONS

The Merck Index, 11th ed. publish 1989 by Merck & Co., Inc. (NJ), p. 1549, monograph #9751.*

* cited by examiner

*Primary Examiner*—Christopher S. F. Low
*Assistant Examiner*—Leslie A. Royds
(74) *Attorney, Agent, or Firm*—Sughrue Mion, PLLC

(57) ABSTRACT

The present invention provides an antioxidative composition with high safety, which is capable of lessening oxidative stress due to active oxygen species, free radicals, or the like in vivo, thereby preventing the occurrence or worsening of a disease. It was confirmed that by using a composition containing oxidized coenzyme Q and/or reduced coenzyme Q, the amount of urinary 8-hydroxydeoxyquanosine can be decreased in normal or diabetic animals. Also, in histopathological research of the spleens of diabetic rats, it was confirmed that spleen tissue denaturation caused by oxidative stress can be prevented. It was thus found that oxidative stress in vivo can be lessened. According to the present invention, oxidative stress in vivo can be lessened by using a composition containing coenzyme Q as an active ingredient.

16 Claims, 3 Drawing Sheets

\* p<0.05 SIGNIFICANT DIFFERENCE FROM SOLVENT CONTROL
(Student t-test)

COMPOSITIONS FOR LESSENING OXIDATIVE STRESS

TECHNICAL FIELD

The present invention relates to an antioxidative composition capable of lessening oxidative stress in vivo.

BACKGROUND ART

In recent years, adverse effects of oxidative stress in vivo, i.e., active oxygen species (hydroxy radicals, alkoxy radicals, hydroperoxy radicals, peroxy radicals, iron-oxygen complexes, superoxides, hydrogen peroxide, hydroperoxides, singlet oxygen, and ozone) or free radicals (lipid radicals and the like) on diseases have been made clear. The most popular theory is that arterial sclerosis is caused by oxidation of low-density lipoproteins (LDL) in the plasma. This theory is that oxidized LDL, i.e., LDL undergoing lipid oxidation due to oxidative stress, causes foaming of macrophages to cause arterial sclerosis. Many researchers have given affirmative reports. Also, the theory is strongly supported by the fact that probucol as a cholesterol decreasing medicine exhibiting an antioxidative activity exhibits effectiveness for arterial sclerosis. Besides arterial sclerosis, the effect of oxidative stress on carcinogenesis, cerebral ischemia, hepatopathy, and the like. Furthermore, there have been reports on many diseases such as diabetes, nervous diseases, renal diseases, hepatic cirrhosis, arthritis, retinopathy of prematurity, ocular uveitis, retinal rust disease, senile cataract, side-effect failures due to radiation therapy, asbestos diseases, bronchial failures due to smoking, anticancer drug side-effect failures, cerebral edema, pulmonary edema, foot edema, cerebral infarction, hemolytic anemia, progeria, epilepsy, Alzheimer disease, Down syndrome, Parkinson disease, Behect's disease, Crohn's disease, Kawasaki disease, Weber-Christian disease, collagen disease, progressive systemic sclerosis, herpetic dermatitis, immune deficiency syndrome, and the like. Although the active oxygen species causing oxidative stress are originally necessary and essential for biological defense, excessive oxidative stress is often present due to reductions of in-vivo antioxidative substances with changes in easting habits or increases in amount of lipids which easily produce release sources of free radicals. According to many researches, it is thought to be nearly certain that the oxidative stress acts as triggers or worsening factors of many diseases. The effectiveness of an antioxidant (radical scavenger) thought to have the ability to eliminate the oxidative stress on the above diseases has studied from old times, and an anti-inflammatory agent exhibiting a radical eliminating ability has been developed. Also, a novel substance (Radicut) exhibiting an antioxidative function has recently been recognized as a medicine. Therefore, it can be said obvious that a substance having an antioxidative function is useful in decreasing oxidative stress. However, such a substance is a medicine, and thus not everybody can use it. Examples of an easily usable substance include antioxidants used for supplements and the like. Namely, the examples include vitamin E, vitamin C, cortisol, β-carotene, vitamin A, BHA (2,6-di-t-butyl-4-methoxyphenol), BHT (2,6-di-t-butyl-4-methylphenol), 7,8-benzoflavone, copper, 3,5-diisopropyl salicylate, and the like. However, the effectiveness of these examples has not yet been known. Conversely, it has been reported that large doses of these antioxidants for increasing the effectiveness produce side effects. For example, with respect to vitamin E, the clinical test results of kidney dialysis patients have recently been reported (Lancet, 356, 1213–1218, 2000). The death rate of kidney dialysis patients by circulatory diseases is 5 to 20 times as high as persons not undergoing kidney dialysis, and oxidative stress is thought to be involved as a factor in this result. This report shows the research result that the rate of coincidence of circulatory diseases was decreased by 10% to 20% by administering vitamin E to a patient in a daily dose of 800 IU (80 to 100 times as large as a normal dose). Also, the report shows that a risk of brain hemorrhage as a side effect of vitamin E was increased by 63%, and two patients died from hemorrhagic diseases. In this report, it is described that the rate of coincidence of circulatory diseases due to oxidative stress can be clearly decreased with vitamin E. The report further shows the risk of side effects of vitamin E and discloses that a further research on the use of vitamin E is required from the viewpoint of side effects. With respect to the side effects of large doses of vitamin E, the American Committee of Fetus and Newborn Pediatrics recommended to stop large doses of vitamin E because many newborn babies died in 1985. At the same time, the side effects of oral administration, such as septicemia, necrotizing colitis, and the like, were thought to be due to overdoses of vitamin E. Also, the side effects of intravenous administration were thought to be due to a synergistic action with a surfactant used for suspending vitamin E (Committee of Fetus and Newborn Pediatrics, 76, 315, 1985; D. L. Phelps, Amer. J. Clin. Nutr., 46, 187, 1987). Furthermore, some doubt is cast on the effects of vitamin C and vitamin A in vivo, and the side effects thereof are also suggested (Kunihiko Sato, Jikken Igaku (Experimental Medicine), 4, 1116, 1986; Y. Oyanagi, Biochem. Pharmacol., 25, 1473, 1976). In this way, under the present circumstances, there are many examples in which a substance exhibiting a strong antioxidative activity in vitro does not necessarily exhibit an effective activity in vivo. The great problem of curing with such an antioxidant is that while it can be expected that an antioxidant can decrease oxidative stress to inhibit the occurrence or worsening of a disease, a dose having the probability of showing effectiveness, i.e., a large dose, causes side effects with a high probability. Therefore, an oxidative stress lessening substance (antioxidant) in vivo, which has high safety and can be safely used, has not yet been found.

SUMMARY OF THE INVENTION

An object of the present invention is to provide an antioxidant with excellent safety, which can lessen oxidative stress in vivo.

As a result of research for solving the above problem, the inventors found that oxidized coenzyme Q and reduced coenzyme Q with high safety have the antioxidative effect of lessening oxidative stress in vivo.

Namely, the present invention relates to a composition for lessening oxidative stress, which comprises coenzyme Q as an active ingredient.

DETAILED DISCLOSURE OF THE INVENTION

A composition for lessening oxidative stress of the present invention comprises, as an active ingredient, coenzyme Q represented by formula (1) and/or formula (2):

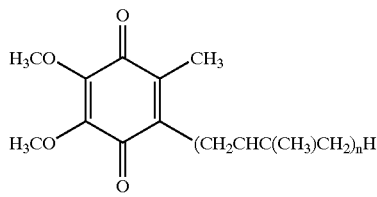

(1)

(wherein n represents an integer from 1 to 12);

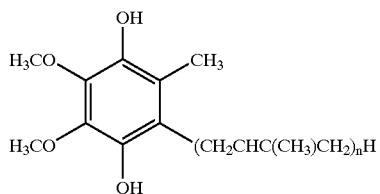

(2)

(wherein n represents an integer from 1 to 12)

Coenzyme Q is an essential component which is distributed in a wide variety of living organisms ranging from bacteria to mammals. It is known that coenzyme Q is present as a constituent in the electron transport system of the mitochondria in the organic cells. It is also known that coenzyme Q undergoes oxidation/reduction cycles in the mitochondria to function as a transfer component in the electron transport system, and reduced coenzyme Q exhibits an antioxidative function in vitro. Human coenzyme Q is mainly composed of coenzyme $Q_{10}$, having 10 repeat structures in its side chain. Although reduced coenzyme $Q_{10}$ exhibits antioxidative activity in vitro, oxidized coenzyme $Q_{10}$ exhibits no antioxidative activity. However, oxidized coenzyme $Q_{10}$ is thought to be converted to a reduced form with a reductase in vivo.

The high safety of coenzyme $Q_{10}$ is regarded as its important characteristic. In a chronic toxicity test of rats, it has been reported that no toxic effect was observed in continuous administration in a daily dose of 1200 mg/kg/day for 52 weeks (K. D. Williams, et al. J. Agric. Food Chem., 47, 3756–3763, 1999). The daily dose of 1200 mg/kg/day is converted into a dose of 60 g/day for human beings (body weight 50 kg). Since a usual dose of coenzyme $Q_{10}$ used as a health food in the United States and Europe is 100 to 300 mg/day, coenzyme $Q_{10}$ is found to be a supplement material having a high safety rate.

Coenzyme Q is represented by formula (1) and/or formula (2):

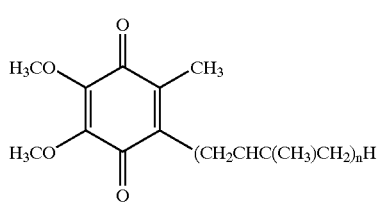

(1)

(wherein n represents an integer from 1 to 12);

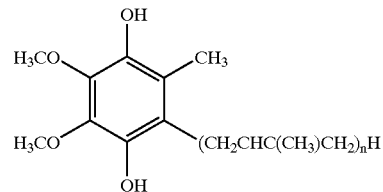

(2)

(wherein n represents an integer from 1 to 12) Oxidized coenzyme Q is represented by formula (1) and reduced coenzyme Q is represented by formula (2).

As shown by the formulae (1) and (2), coenzyme Q having 1 to 12 repeat units (n in each formula) in its side chain can be used in the present invention. Particularly, coenzyme Q having 10 repeat units in its side chain, i.e., coenzyme $Q_{10}$, can be preferably used.

The method for producing oxidized coenzyme Q and reduced coenzyme Q is not particularly limited. For example, an adaptable method comprises producing coenzyme Q by a conventional known method such as synthesis, fermentation or extraction from a natural resource, and then concentrating an oxidized coenzyme Q fraction or reduced coenzyme Q fraction of from a chromatography eluate. Oxidized coenzyme Q can be obtained by a known method. On the other hand, when reduced coenzyme Q is desired, a general reducing agent such as sodium borohydride, sodium dithionite (sodium hydrosulfite), or the like may be added to the coenzyme Q according to demand to reduce the coenzyme Q to reduced coenzyme Q by a conventional method, and then the reduced coenzyme Q may be concentrated by chromatography. Also, reduced coenzyme Q can be obtained by a method in which existing high-purity coenzyme Q is reacted with a reducing agent.

In the present invention, a reduced form and an oxidized form may be singly used as coenzyme Q, or a mixture of the oxidized form and reduced form may be used. In the use of coenzyme $Q_{10}$, a mixture of the reduced form and oxidized form has higher oral absorptivity than that of the use of only the oxidized form (Publication WO98/07417), and thus coenzyme $Q_{10}$ containing the reduced form is preferably used as an oral agent. In this case, from the viewpoint of oral absorptivity the ratio of reduced coenzyme $Q_{10}$ in the total of coenzyme $Q_{10}$ is preferably 20% by weight or more, more preferably 40% by weight or more, and most preferably 60% by weigh or more. Although the upper limit of the ratio is not limited, the upper limit is generally 99% by weight or less.

Although the total content of coenzyme Q in the composition of the present invention is not particularly limited, the content is preferably from 0.001% by weight to 99% by weight, and more preferably from 0.01% by weight to 20% by weight, from the viewpoint of effectiveness.

Besides the coenzyme Q, the composition of the present invention may contain various additives allowable in the medical field or Food Sanitation Law. When the composition is used as a countermeasure against one of various diseases, the composition can be used in a combination with a medicine for a disease. Furthermore, another antioxidant, a health food material, a supplement material and vitamin may be added. Since reduced coenzyme Q is known to have the ability to reproduce vitamin E, a combination of reduced coenzyme Q and vitamin E is expected to show a synergistic function.

The administration form of the composition of the present invention may be a liquid or a solid, and the administration method may be any one of various methods such as oral administration, administration of an injection, nasal drops, eye drops, or a suppository, eating of coenzyme Q-containing food, and the like. Generally, oral administration is though to be effective from the viewpoint of dosage. However, when the composition is used for a local disease or when oral administration is difficult, there is no problem in any administration method of the composition of the present invention, other than oral administration. Conceivable examples of such an administration method include administration of eye drops for preventing diabetic retinopathy, administration of a suppository to a patient, an elderly person or an infant who has a difficulty in oral administration of nutrients, administration of an external preparation for skin diseases, and the like. However, the administration method is not limited to these examples.

The composition of the present invention can be produced by adding coenzyme Q as the active ingredient, and adding various additives according to demand.

In the oral administration of the composition of the present invention, the dose of coenzyme Q per kg of weight of a human body is preferably from 0.1 mg/day to 500 mg/day, more preferably from 1 mg/day to 100 mg/day, and most preferably from 2 mg/day to 75 mg/day.

The composition of the present invention has the antioxidative function to lessen oxidative stress in vivo. The in-vivo antioxidative function of coenzyme Q was discovered in the present invention for the first time. Therefore, the composition of the present invention is effective in curing and/or preventing diseases due to oxidative stress.

As described above, coenzyme $Q_{10}$, which is a type of enzyme Q, has high safety, and thus the in-vivo use of the composition containing coenzyme $Q_{10}$ has no danger of side effects. This property is not exhibited by vitamin E known to have the same antioxidative function, and thus the property can be regarded as an excellent characteristic of the composition of the present invention.

BEST MODE FOR CARRYING OUT THE INVENTION

Although the present invention will be described in further detail below with reference to examples, the present invention is not limited to these examples.

The effect of lessening oxidative stress in vivo was evaluated with urinary 8-hydroxydeoxyguanosine (8OH-dG) having high effectiveness as an oxidative stress marker. This material results from nucleic acid damage due to oxidative stress, and is discharged into urine without undergoing further metabolism. It is thus thought that the amount of oxidative stress in vivo and the amount of 8OH-dG discharged have a close relationship therebetween. A decrease in amount of the material in urine means a reduction in oxidative stress in vivo and the prevention of damage to nucleic acid.

EXAMPLE 1

Oxidative Stress Lessening Effect on Normal Rat

Figure 1:
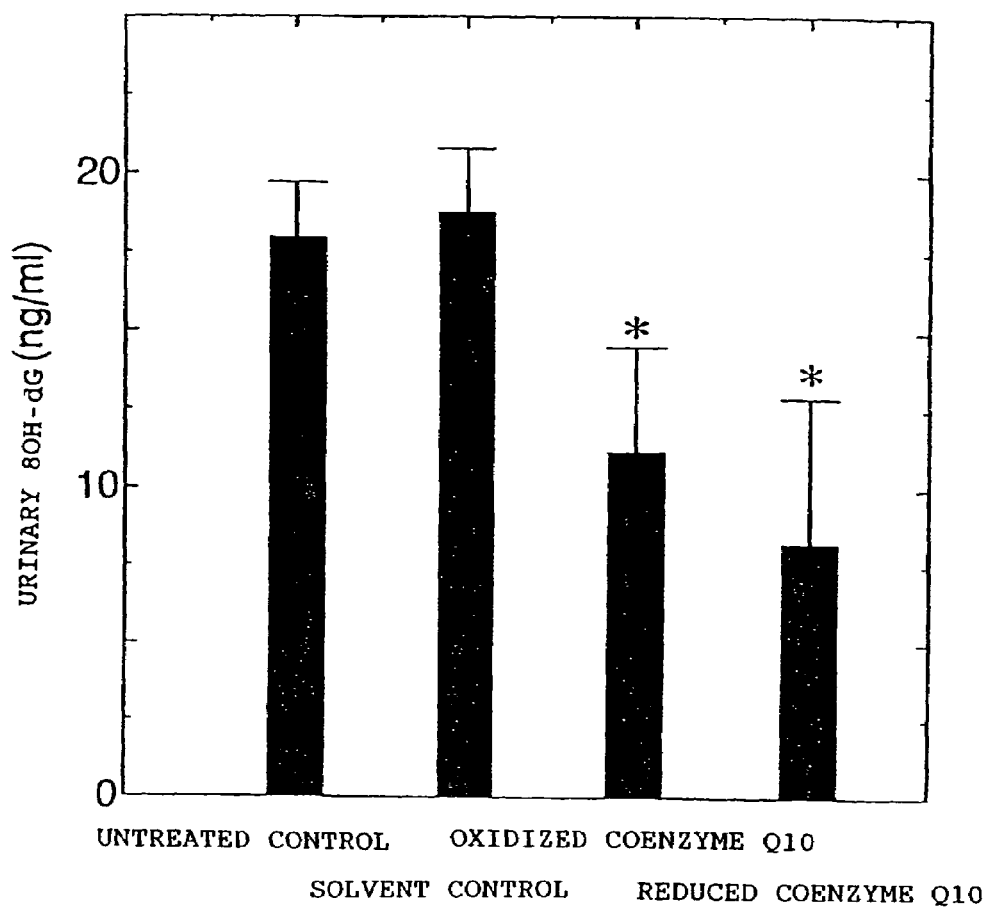
FIG. 1 is a bar graph showing the amounts of urinary 8OH-dG of SD rats administered with reduced or oxidized coenzyme $Q_{10}$, in which the amount of urinary 8OH-dG is shown as ordinate, data of average±SD with n=3 is shown, and * shows significance against a control group with a risk rate of 5% in a Student t-test carried out as a significant difference test.

A soybean oil solution of oxidized coenzyme $Q_{10}$ or reduced coenzyme $Q_{10}$ (containing about 2% of oxidized coenzyme $Q_{10}$) was orally administered to SD rats (6-week old, male) in a dose of 100 mg/kg/day for 4 weeks. 4 weeks after, urine was collected, and the amount of urinary 8OH-dG was determined by an ELISA kit (Japan Institute for the Control of Aging). The results are shown in FIG. 1. In the oxidized coenzyme $Q_{10}$ administration group, the amount of urinary 8OH-dG was significantly decreased to about 60% of that of the solvent control group (urinary 8OH-dG was assumed as 100%). In the reduced coenzyme $Q_{10}$ administration group, the amount of urinary 8OH-dG was significantly decreased to about 40% of that of the solvent control group.

EXAMPLE 2

Oxidative Stress Lessening Effect on Spontaneously Diabetic Rat

Figure 2:
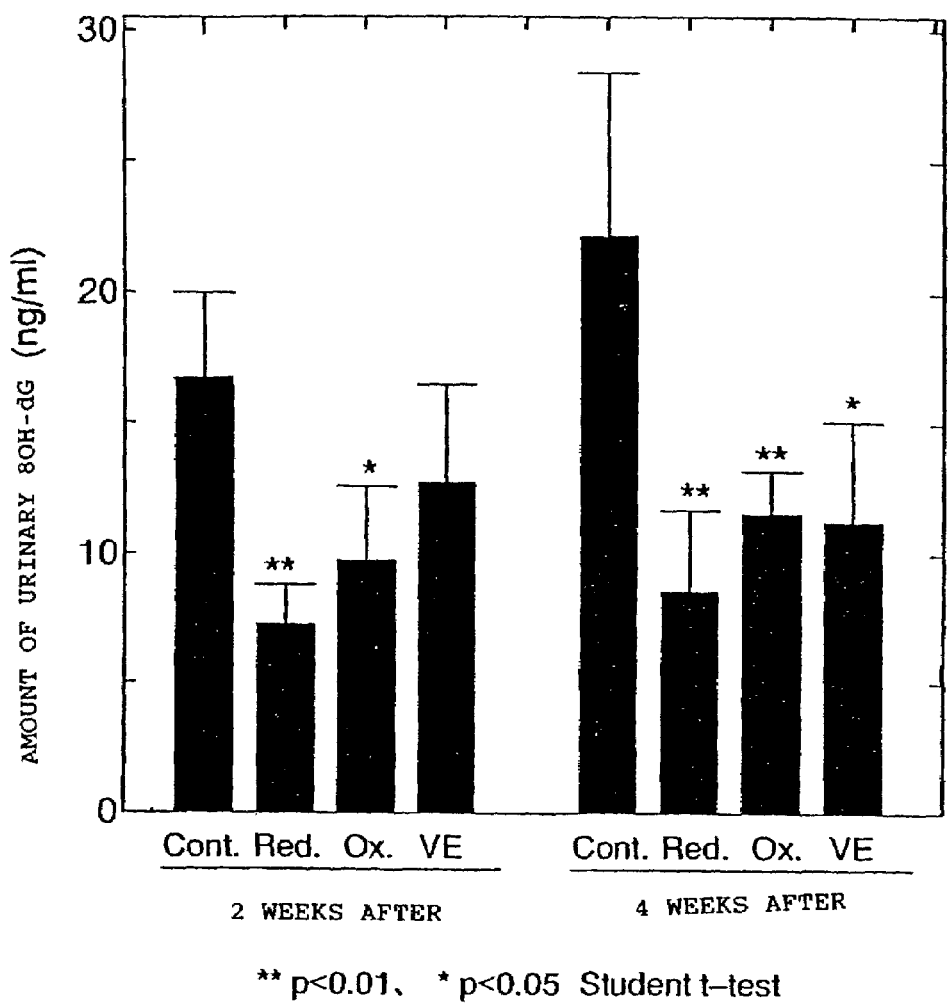
FIG. 2 is a bar graph showing the amounts of urinary 8OH-dG of GK rats administered with reduced or oxidized coenzyme $Q_{10}$, in which the amount of urinary 8OH-dG is shown as ordinate, data of average±SD with n=4 is shown. In the figure, Cont. represents a control group, Red. represents a reduced coenzyme $Q_{10}$ administration group, Ox represents an oxidized coenzyme $Q_{10}$ administration group, and VE represents a vitamin E administration group. In the graph, values measured 2 weeks after the administration are shown in the left half, and values measured 4 weeks after the administration are shown in the right half. In the graph, ** and * show significance against a control group with risk rates of 1% and 5%, respectively, in a Student t-test carried out as a significant difference test.

The oxidative stress lessening effect of each of reduced and oxidized coenzyme $Q_{10}$ in vivo was evaluated by using GK rats with spontaneous diabetes which induced spleen tissue denaturation due to oxidative stress in vivo. A feed (CE-2, produced by CLEA JAPAN, INC.) containing 0.1% by weight of reduced coenzyme $Q_{10}$ (containing about 2% by weight of oxidized coenzyme $Q_{10}$) or oxidized coenzyme $Q_{10}$ was freely given to GK rats (5-week old, male, n=4 in each group). In a control group, the feeds not containing coenzyme $Q_{10}$ was freely given to the rats. 2 weeks and 4 weeks after, urine was collected, and the amount of urinary 8OH-dG was determined by the same method as in Example 1. The results are shown in FIG. 2. In the reduced coenzyme $Q_{10}$ administration group, the amount of urinary 8OH-dG measured 2 weeks after the administration was significantly decreased to about 40% of that of the control group (urinary 8OH-dG was assumed as 100%), and the amount of urinary 8OH-dG measured 4 weeks after the administration was kept at the same level. In the oxidized coenzyme $Q_{10}$ administration group, the amount of urinary 8OH-dG measured 2 weeks after the administration was decreased to 58% of the control group, and the amount of urinary 8OH-dG measured 4 weeks after the administration was deceased to 52% of the control group. Although the amounts of urinary 8OH-dG in the oxidized coenzyme $Q_{10}$ administration group were larger than those in the reduced coenzyme $Q_{10}$ administration group, the amounts of urinary 8OH-dG were significantly decreased in comparison to the control group.

REFERENCE EXAMPLE 1

Oxidative Stress Lessening Effect of Vitamin E on Spontaneously Diabetic Rat

The oxidative stress lessening effect of a typical antioxidant, vitamin E, was evaluated by using GK rats in the same test system as in Example 2. Like coenzyme $Q_{10}$, vitamin E was mixed with a feed at a ratio of 0.1% by weight, and the resulting foodstuff was freely given to the GK rats. 2 weeks and 4 weeks after the feeding, the amount of urinary 8OH-dG was determined. The results are shown in FIG. 2. In the vitamin administration group, the amount of urinary 8OH-dG measured 2 weeks after the administration was decreased to about 80% of that of the control group, and only a downward tendency was exhibited. The amount of urinary 8OH-dG measured 4 weeks after the administration was significantly decreased to 51%. In comparison to the coenzyme $Q_{10}$ administration group of Example 2, 2 weeks after, the decreasing effect in Reference Example 1 was lower the effects of both the reduced form and the oxidized form in Example 2, and 4 weeks after, the effect was at the same level as that of the oxidized coenzyme $Q_{10}$ and lower than that of the reduced coenzyme $Q_{10}$ in Example 2. These results indicate that vitamin E requires much time for expressing antioxidative activity, as compared with coenzyme $Q_{10}$.

EXAMPLE 3

Oxidative Stress Lessening Effect on Spontaneously Diabetic Mouse

Figure 3:
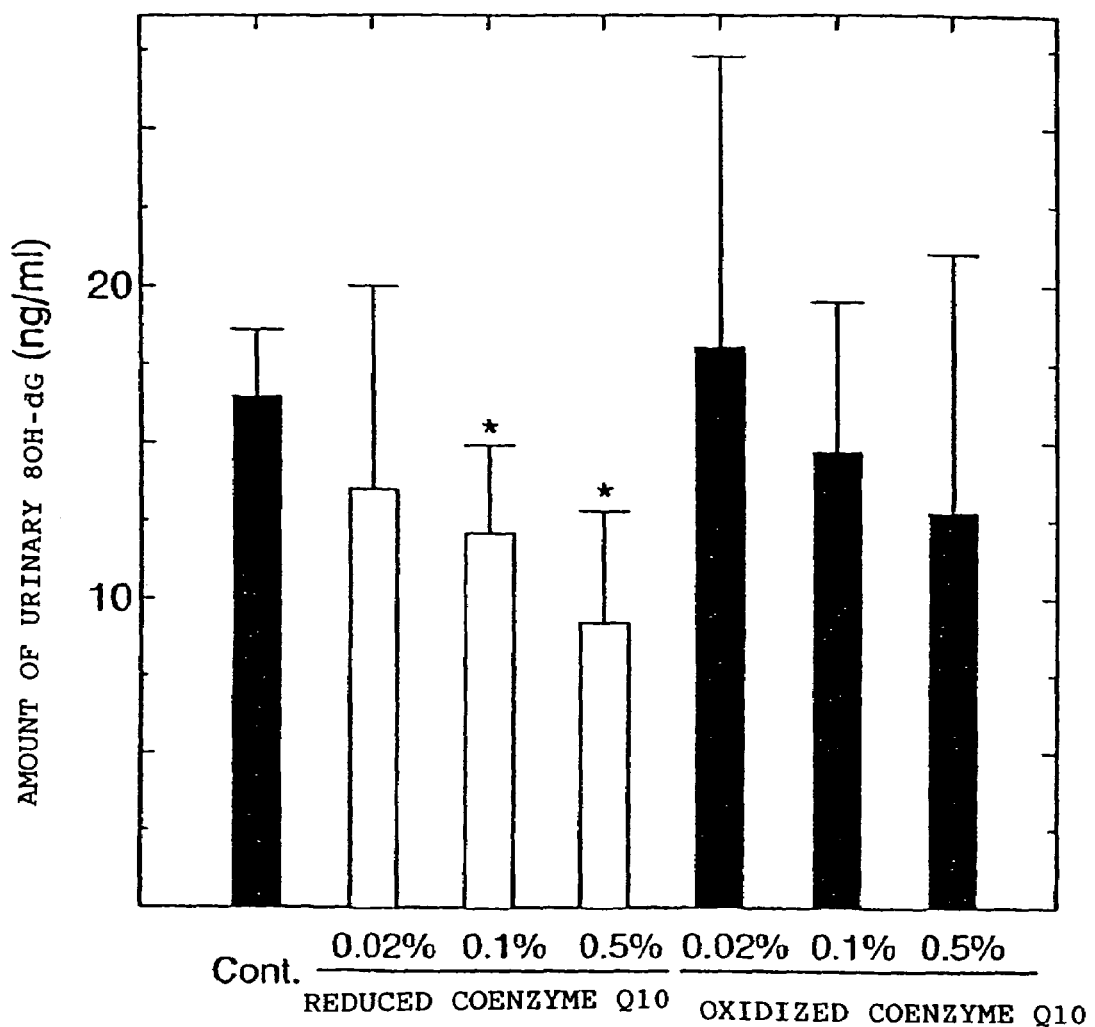
FIG. 3 is a bar graph showing the amounts of urinary 8OH-dG of KK-Ay mice administered with reduced or oxidized coenzyme $Q_{10}$ in which the amount of urinary 8OH-dG is shown as ordinate, data of average±SD with n=11 is shown, and * shows significance against a control group with a risk rate of 5% in a Student t-test carried out as a significant difference test.

The dose dependency of the oxidative stress lessening effect of each of reduced and oxidized coenzyme $Q_{10}$ was evaluated by the same method as that used for GK rats except that KK-Ay mice with spontaneous diabetes and having a higher blood sugar level than that of GK rats were used. KK-Ay 5-week old male mice were used, and evaluated in groups in each of which n=11. Oxidized coenzyme $Q_{10}$ or reduced coenzyme $Q_{10}$ (containing about 2% by weight of oxidized coenzyme $Q_{10}$) was mixed with a purified feed (produced by CLEA JAPAN, INC.) at each of ratios of 0.02% by weight, 0.1% by weight, and 0.5% by weight, and each mixture was freely given to the KK-Ay mice. In a control group, the purified feed not containing coenzyme $Q_{10}$ was freely given to rats. 4 weeks after the supply, urine was collected, and the amount of urinary 8OH-dG was determined by the same method as in Example 1. The results are shown in FIG. 3. Both the reduced coenzyme $Q_{10}$ and the oxidized coenzyme $Q_{10}$ exhibited the dose-dependent oxidative stress lessening effect, as compared with the control group. In the reduced coenzyme $Q_{10}$ administration group, with a dose of 0.02% by weight, the lessening effect was low (82% of the control group), while with a dose of 0.1% by weight or more, the lessening effect was significant (dose of 0.1% by weight: 73% of the control group, dose of 0.5% by weight: 56% of the control group).

In the oxidized coenzyme $Q_{10}$ administration group, the dose-dependent lessening effect was observed without showing a significant difference, and with a dose of 0.5% by weight, the amount of urinary 8OH-dG was 78% of that of the control group.

As described above, the oxidative stress lessening effect of coenzyme $Q_{10}$ in vivo was confirmed with normal rats, spontaneously diabetic rats and spontaneously diabetic mice. Also, in any one of the tests, the effect of the reduced form was higher than that of the oxidized form, and the effectiveness of reduced coenzyme $Q_{10}$ is expected.

Also, the GK rats used in Example 2 are known to have the spleen tissue damaged by oxidative stress, and thus evaluation was made for the protective effect of decreasing oxidative stress by coenzyme $Q_{10}$ to protect GK rats from denaturation of the spleen tissues.

EXAMPLE 4

Tissue Protecting Effect on Spontaneously Diabetic Rat

The protective effect of each of oxidized coenzyme $Q_{10}$ and reduced coenzyme $Q_{10}$ (containing about 2% by weight of oxidized coenzyme $Q_{10}$) on denaturation of the spleen tissues of GK rats by using the same test system as in Example 1. As a control, a soybean oil solution not containing coenzyme $Q_{10}$ was orally administered. After the coenzyme $Q_{10}$ was administered for 7 weeks, the spleen was extracted from each rat, and the degree of tissue denaturation was histopathologically evaluated. The results are shown in Table 1.

TABLE 1

| | Number of examples | | | |
| --- | --- | --- | --- | --- |
| Findings | Control | Reduced coenzyme $Q_{10}$ | Oxidized coenzyme $Q_{10}$ | VE |
| Normal | 0 | 0 | 0 | 0 |
| Islet fibrillation 1+ | 0 | 3 | 2 | 2 |
| Islet fibrillation 2+ | 4 | 1 | 2 | 2 |

Islet fibrillation = fibrillation of the Langerhans' islet tissue

The fibrillation of the Langerhans' islet tissue known to secrete insulin was observed for the spleens. In the control group, fibrillation at a degree of +2 (higher than a degree of +1) was observed in all of the four examples. In the reduced coenzyme $Q_{10}$ administration group, fibrillation at a degree of +1 was observed in tree examples, and fibrillation at a degree of +2 was observed in one example. Namely, the tendency to decrease fibrillation was observed. In the oxidized coenzyme $Q_{10}$ administration group, fibrillation at a degree of +1 was observed in two examples, and fibrillation at a degree of +2 was observed in two examples. Namely, the tissue denaturation due to oxidative stress was decreased, as compared with the control group. However, the protective effect of the oxidized coenzyme $Q_{10}$ administration group was slightly lower than that of the reduced coenzyme $Q_{10}$ administration group.

REFERENCE EXAMPLE 2

Tissue Protecting Effect of Vitamin E on Spontaneously Diabetic Rat

The tissue protecting effect of vitamin E was evaluated by the same method as in Example 4. As a result, fibrillation at a degree of +1 was observed in two examples, and fibrillation at a degree of +2 was observed in two examples, as shown in Table 1. Therefore, the results were the same as oxidized coenzyme $Q_{10}$, and tissue denaturation was decreased in comparison to the control group. However, the tissue protecting effect of vitamin E was slightly lower than that of the reduced coenzyme $Q_{10}$ administration group.

As a result of the evaluation of the protective effect of each of oxidized coenzyme $Q_{10}$ and reduced coenzyme $Q_{10}$ on denaturation of the spleen tissues of the GK rats, it was found that tissue denaturation is decreased by administering coenzyme $Q_{10}$, and the protective function of reduced coenzyme $Q_{10}$ is higher than that of oxidized coenzyme $Q_{10}$. The protective effect on fibrillation of the spleen Langerhans' islet tissue of a GK rat is caused by a decrease in oxidative stress due to oxidized coenzyme $Q_{10}$ and reduced coenzyme $Q_{10}$ in vivo. The result indicates that coenzyme $Q_{10}$ is useful as a substance (antioxidant) for lessening oxidative stress in vivo. As a result of the evaluation of vitamin E which is a typical existing antioxidant, and comparison to coenzyme $Q_{10}$, the activity to decrease the amount of 8OH-dG and the activity to protect the spleen tissue from fibrillation were observed. However, both activities of vitamin E were at the same level as or lower than those of oxidized coenzyme $Q_{10}$, and were clearly lower than those of reduced coenzyme $Q_{10}$.

As described above, vitamin E uncertainly exhibits effectiveness for human beings. However, the possibility of the side effects increases as the dose increases, thereby causing difficulty in achieving a secured effect. On the other hand, the high safety of coenzyme $Q_{10}$ was proved, and coenzyme $Q_{10}$ exhibits an in-vivo antioxidative activity equal to or higher than that of vitamin E and significantly decreases oxidative stress in vivo. It is thus decided that coenzyme $Q_{10}$ is an antioxidant useful for various diseases caused by oxidative stress or worsened by oxidative stress.

INDUSTRIAL APPLICABILITY

The composition of the present invention comprising coenzyme Q as an active ingredient decreases oxidative stress in vivo, and exhibits an excellent effect on many diseases and health maintenance.

What is claimed is:

1. A composition for lessening oxidative stress, comprising, as an active ingredient, coenzyme Q represented by formula (1) and formula (2), the coenzyme Q of formula (2) being present in an amount of 0.1% by weight to 0.5% by weight, based on the weight of the composition:

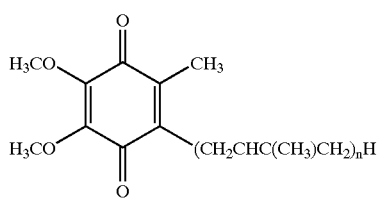

(wherein n represents an integer from 1 to 12);

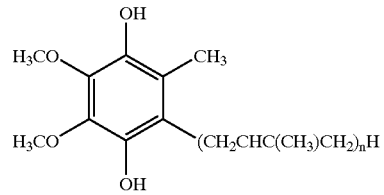

(wherein n represents an integer from 1 to 12).

2. The composition according to claim 1, wherein the coenzyme Q of formula (1) and (2) is coenzyme $Q_{10}$.

3. A method for lessening oxidative stress in vivo in a subject in need thereof, comprising administering to said subject a composition containing a reduced coenzyme Q of formula (2) and an oxidized coenzyme Q of formula (1), he coenzyme Q of formula (2) being present in an amount of 0.1% by weight to 0.5% by weight, based on the weight of the composition:

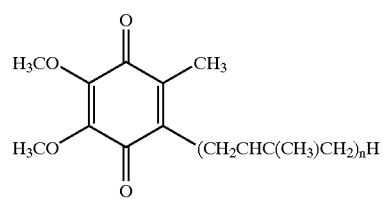

(wherein n represents an integer from 1 to 12);

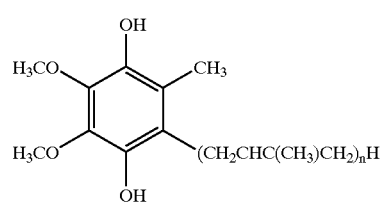

(wherein n represents an integer from 1 to 12).

4. A method for reducing oxidative stress associated with a disease in vivo comprising administering to a subject a composition containing a reduced coenzyme Q antioxidant of formula (2) and an oxidized coenzyme Q of formula (1), the coenzyme Q of formula (2) being present in an amount of 0.1% by weight to 0.5% by weight, based on the weight of the composition:

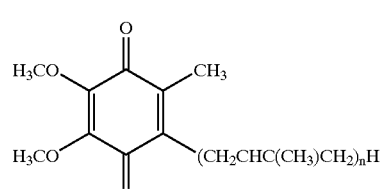

(wherein n represents an integer from 1 to 12);

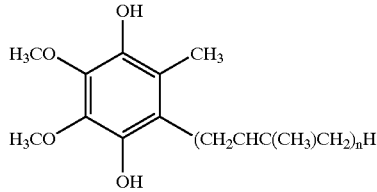

(wherein n represents an integer from 1 to 12).

5. A method for according to claim 4, wherein the disease is selected from the group consisting of cerebral ischemia, hepatopathy, diabetes, nervous diseases, renal diseases, hepatic cirrhosis, arthritis, retinopathy of prematurity, ocular uveitis, retinal rust disease, senile cataract, asbestos diseases, bronchial failures due to smoking, cerebral edema, pulmonary edema, foot edema, cerebral infarction, hemolytic anemia, progeria, epilepsy, Behect's disease, Crohn's disease, Kawasaki disease, Weber-Christian disease, collagen disease, progressive systemic sclerosis, herpetic dermatitis and immune deficiency syndrome.

6. A method according to claim 4, wherein the reduced and oxidized coenzyme Q are administered to a human in a total dose per kg of weight of a human body of 0.1 mg/day to 500 mg/day.

7. A method according to claim 4, wherein the reduced and oxidized coenzyme Q are administered to a human in a total dose per kg of weight of a human body of 1 mg/day to 100 mg/day.

8. A method according to claim 4, wherein the reduced and oxidized coenzyme Q are administered to a human in a total dose per kg of weight of a human body of 2 mg/day to 75 mg/day.

9. A method for reducing oxidative stress in vivo due to a skin disease comprising externally administering to a subject a composition containing a reduced coenzyme Q of formula (2) and an oxidized coenzyme Q of formula (1) the coenzyme Q of formula (2) being present in an amount of 0.1% by weight to 0.5% by weight, based on the weight of the composition:

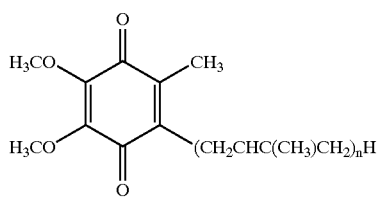

(wherein n represents an integer from 1 to 12);

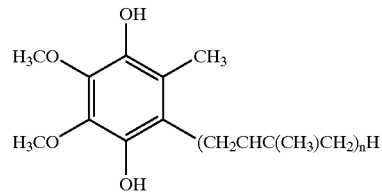

(wherein n represents an integer from 1 to 12).

10. A method for lessening oxidative stress in vivo in a subject in need thereof, comprising administering to said subject a composition containing a reduced coenzyme Q of formula (2), the coenzyme Q of formula (2) being present in an amount of 0.1% by weight to 0.5% by weight, based on the weight of the composition:

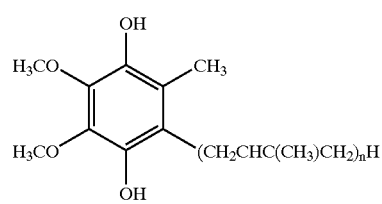

(wherein n represents an integer from 1 to 12).

11. A method for reducing oxidative stress in vivo due to a skin disease comprising administering to a subject a composition containing a reduced coenzyme Q antioxidant of formula (2), the coenzyme Q of formula (2) being present in an amount of 0.1% by weight to 0.5% by weight, based on the weight of the composition:

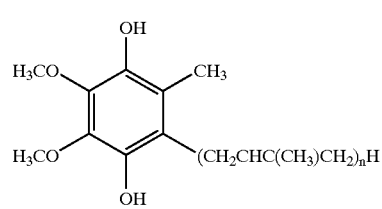

(wherein n represents an integer from 1 to 12).

12. A method according to claim 11, wherein the disease is selected from the group consisting of cerebral ischemia, hepatopathy, diabetes, nervous diseases, renal diseases, hepatic cirrhosis, arthritis, retinopathy of prematurity, ocular uveitis, retinal rust disease, senile cataract, asbestos diseases, bronchial failures due to smoking, cerebral edema, pulmonary edema, foot edema, cerebral infarction, hemolytic anemia, progeria, epilepsy, Behect's disease, Crohn's disease, Kawasaki disease, Weber-Christian disease, collagen disease, progressive systemic sclerosis, herpetic dermatitis and immune deficiency syndrome.

13. A method according to claim 11, wherein the reduced coenzyme Q is administered to a human in dose per kg of weight of a human body of 0.1 mg/day to 500 mg/day.

14. A method according to claim 11, wherein the reduced coenzyme Q is administered to a human in dose per kg of weight of a human body of 1 mg/day to 100 mg/day.

15. A method according to claim 11, wherein the reduced coenzyme Q is administered to a human in dose per kg of weight of a human body of 2 mg/day to 75 mg/day.

16. A method for reducing oxidative stress due to a skin disease in vivo comprising externally administering to a subject a composition containing a reduced coenzyme Q of formula (2), the coenzyme Q of formula (2) being present in an amount of 0.1% by weight to 0.5% by weight, based on the weight of the composition:

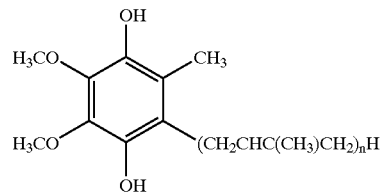

(2)

(wherein n represents an integer from 1 to 12).

* * * * *